(12) United States Patent
Taylor et al.

(10) Patent No.: US 6,300,081 B1
(45) Date of Patent: *Oct. 9, 2001

(54) ACTIVATED RAS INTERACTION ASSAY

(75) Inventors: Stephen J. Taylor, Ithaca; David Shalloway, Spencer, both of NY (US)

(73) Assignee: Cornell Research Foundation, Inc., Ithaca, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/971,207

(22) Filed: Nov. 14, 1997

Related U.S. Application Data
(60) Provisional application No. 60/030,924, filed on Nov. 15, 1996.

(51) Int. Cl.[7] .............................. C12Q 1/00; C12Q 1/24; G01N 33/53; G01N 33/567

(52) U.S. Cl. .......................... 435/7.1; 435/4; 435/7.21; 435/7.23; 435/30; 435/320; 424/130.1; 424/133.1; 424/134.1; 436/536; 530/350; 530/380; 530/385; 530/386; 530/387.1; 530/389.1

(58) Field of Search .................. 424/130.1, 133.1, 424/134.1; 530/387.1, 389.1, 350, 380, 385, 386; 435/4, 7.1, 30, 7.21, 7.23, 320.1; 436/536

(56) References Cited

U.S. PATENT DOCUMENTS

| | | |
|---|---|---|
| 4,877,867 | 10/1989 | Shalitin . |
| 4,957,859 | 9/1990 | Bizub et al. . |
| 5,068,175 | 11/1991 | Prashad . |
| 5,156,841 | 10/1992 | Rapp . |
| 5,300,631 | 4/1994 | Weinberg et al. . |
| 5,320,947 | 6/1994 | Cheever et al. . |
| 5,352,660 | 10/1994 | Pawson . |
| 5,405,941 | 4/1995 | Johnson . |
| 5,434,064 | 7/1995 | Schlessinger et al. . |
| 5,443,956 | 8/1995 | Carney . |

FOREIGN PATENT DOCUMENTS

| | | |
|---|---|---|
| 535 663 A2 | 4/1993 | (EP) . |
| 605 789 A1 | 7/1994 | (EP) . |
| 646 64 A2 | 4/1995 | (EP) . |
| WO89/10565 * | 11/1989 | (WO) ................................ 435/7.23 |
| WO 94/28009 | 12/1994 | (WO) . |

OTHER PUBLICATIONS

DiBattiste et al., "Difference in the Interaction of p21[c-Ha-ra]s-GMP-PNP With Full Length Neurofibromin and GTPase-Activating Protein," *Oncogene*, 8:637–643 (1993).

Jelinek et al., "RAS and RAF-1 Form a Signaling Complex With MEK-1 But Not MEK-2," *Molecular and Cellualr Biology*, 14(12):8212–8218 (1994).

Hudson et al., "Screening Method for Identifying Inhibitors of Ras-Protein Partner Interacitons," *Research Disclosure*, 371(37134):158 (1995).

Ghosh et al., "The Cysteine-Rich region of Raf-1 Kinase Contains Zinc, Translocates to Liposomes, and is Adjacent to a Segment That Binds GTP-Ras," *J. Biol. Chem.*, 269(13):10000–7 (1994).

Chuang et al., "Critical Binding and Regulatory Interactions Between Ras and Raf Occur Through a Small, Stable N-Terminal Domain of Raf and Specific Ras Effector Residues," *Mol. Cell. Biol.*, 14(8):5318–25 (1994).

Warne et al., "Direct Interaction of Ras and the Amino-Terminal Region of Raf-1 In Vitro," *Nature*, 364:352–55 (1993).

Yamamori et al., "Purification of a Ras-Dependent Mitogen-Activated ProteinKinase Kinase Kinase from Bovine Brain Cytosol and its Identification as a Complex of B-Raf and 14–3–3 Proteins," *J. Biol. Chem.*, 270(20):11723–26 (1995).

Freed et al., "Binding of 14–3–3 Proteins to the Protein Kinase Raf and Effects on its Activation," *Science*, 265:1713–16 (1994).

Brtva et al., "Two Distinct Raf Domains Mediate Interaction with Ras," *J. Biol. Chem.*, 270(17):9809–12 (1995).

Radziwill et al., "Direct Interaction and N-Terminal Phosphorylation of c-Jun by c-Mil/Raf," *Proc. Natl. Acad. Sci. USA*, 92:1421–25 (1995).

Niehof et al., "A Small Peptide Derived from the Aminoterminus of c-Raf-1 Inhibits c-Raf/Ras Binding," *Biochemical and Biophysical Research Communications*, 206(1):46–50 (1995).

* cited by examiner

*Primary Examiner*—Sheela Huff
*Assistant Examiner*—Alana M. Harris
(74) *Attorney, Agent, or Firm*—Nixon Peabody LLP

(57) ABSTRACT

The present invention reates to a method for detecting activated ras protein. The method includes immobilizing a protein on a solid support, incubating the immobilized protein with lysates from cultured cells, where the lysates include activated ras protein, and determining the amount of activated ras protein bound to the immobilized protein. The present invention also relates to a method of detecting ras oncogenic related malignancy in a human subject.

24 Claims, 6 Drawing Sheets

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 648 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:1:

```
Met Glu His Ile Gln Gly Ala Trp Lys Thr Ile Ser Asn Gly Phe Gly
 1               5                  10                  15

Phe Lys Asp Ala Val Phe Asp Gly Ser Ser Cys Ile Ser Pro Thr Ile
                20                  25                  30

Val Gln Gln Phe Gly Tyr Gln Arg Arg Ala Ser Asp Asp Gly Lys Leu
            35                  40                  45

Thr Asp Pro Ser Lys Thr Ser Asn Thr Ile Arg Val Phe Leu Pro Asn
        50                  55                  60

Lys Gln Arg Thr Val Val Asn Val Arg Asn Gly Met Ser Leu His Asp
65                  70                  75                  80

Cys Leu Met Lys Ala Leu Lys Val Arg Gly Leu Gln Pro Glu Cys Cys
                85                  90                  95

Ala Val Phe Arg Leu Leu His Glu His Lys Gly Lys Lys Ala Arg Leu
```

-continued

```
                   100                 105                 110
Asp Trp Asn Thr Asp Ala Ala Ser Leu Ile Gly Glu Glu Leu Gln Val
               115                 120                 125
Asp Phe Leu Asp His Val Pro Leu Thr Thr His Asn Phe Ala Arg Lys
           130                 135                 140
Thr Phe Leu Lys Leu Ala Phe Cys Asp Ile Cys Gln Lys Phe Leu Leu
145                 150                 155                 160
Asn Gly Phe Arg Cys Gln Thr Cys Gly Tyr Lys Phe His Glu His Cys
                   165                 170                 175
Ser Thr Lys Val Pro Thr Met Cys Val Asp Trp Ser Asn Ile Arg Gln
               180                 185                 190
Leu Leu Leu Phe Pro Asn Ser Thr Ile Gly Asp Ser Gly Val Pro Ala
           195                 200                 205
Leu Pro Ser Leu Thr Met Arg Arg Met Arg Glu Ser Val Ser Arg Met
    210                 215                 220
Pro Val Ser Ser Gln His Arg Tyr Ser Thr Pro His Ala Phe Thr Phe
225                 230                 235                 240
Asn Thr Ser Ser Pro Ser Ser Glu Gly Ser Leu Ser Gln Arg Gln Arg
                   245                 250                 255
Ser Thr Ser Thr Pro Asn Val His Met Val Ser Thr Thr Leu Pro Val
               260                 265                 270
Asp Ser Arg Met Ile Glu Asp Ala Ile Arg Ser His Ser Glu Ser Ala
           275                 280                 285
Ser Pro Ser Ala Leu Ser Ser Ser Pro Asn Asn Leu Ser Pro Thr Gly
       290                 295                 300
Trp Ser Gln Pro Lys Thr Pro Val Pro Ala Gln Arg Glu Arg Ala Pro
305                 310                 315                 320
Val Ser Gly Thr Gln Glu Lys Asn Lys Ile Arg Pro Arg Gly Gln Arg
                   325                 330                 335
Asp Ser Ser Tyr Tyr Trp Glu Ile Glu Ala Ser Glu Val Met Leu Ser
               340                 345                 350
Thr Arg Ile Gly Ser Gly Ser Phe Gly Thr Val Tyr Lys Gly Lys Trp
           355                 360                 365
His Gly Asp Val Ala Val Lys Ile Leu Lys Val Val Asp Pro Thr Pro
       370                 375                 380
Glu Gln Phe Gln Ala Phe Arg Asn Glu Val Ala Val Leu Arg Lys Thr
385                 390                 395                 400
Arg His Val Asn Ile Leu Leu Phe Met Gly Tyr Met Thr Lys Asp Asn
                   405                 410                 415
Leu Ala Ile Val Thr Gln Trp Cys Glu Gly Ser Ser Leu Tyr Lys His
               420                 425                 430
Leu His Val Gln Glu Thr Lys Phe Gln Met Phe Gln Leu Ile Asp Ile
           435                 440                 445
Ala Arg Gln Thr Ala Gln Gly Met Asp Tyr Leu His Ala Lys Asn Ile
       450                 455                 460
Ile His Arg Asp Met Lys Ser Asn Asn Ile Phe Leu His Glu Gly Leu
465                 470                 475                 480
Thr Val Lys Ile Gly Asp Phe Gly Leu Ala Thr Val Lys Ser Arg Trp
                   485                 490                 495
Ser Gly Ser Gln Gln Val Glu Gln Pro Thr Gly Ser Val Leu Trp Met
               500                 505                 510
Ala Pro Glu Val Ile Arg Met Gln Asp Asn Asn Pro Phe Ser Phe Gln
           515                 520                 525
```

-continued

```
Ser Asp Val Tyr Ser Tyr Gly Ile Val Leu Tyr Glu Leu Met Thr Gly
    530                 535                 540

Glu Leu Pro Tyr Ser His Ile Asn Asn Arg Asp Gln Ile Ile Phe Met
545                 550                 555                 560

Val Gly Arg Gly Tyr Ala Ser Pro Asp Leu Ser Lys Leu Tyr Lys Asn
                565                 570                 575

Cys Pro Lys Ala Met Lys Arg Leu Val Ala Asp Cys Val Lys Lys Val
                580                 585                 590

Lys Glu Glu Arg Pro Leu Phe Pro Gln Ile Leu Ser Ser Ile Glu Leu
    595                 600                 605

Leu Gln His Ser Leu Pro Lys Ile Asn Arg Ser Ala Ser Glu Pro Ser
    610                 615                 620

Leu His Arg Ala Ala His Thr Glu Asp Ile Asn Ala Cys Thr Leu Thr
625                 630                 635                 640

Thr Ser Pro Arg Leu Pro Val Phe
                645
```

(2) INFORMATION FOR SEQ ID NO:2:

(i) SEQUENCE CHARACTERISTICS:
        (A) LENGTH: 149 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Glu His Ile Gln Gly Ala Trp Lys Thr Ile Ser Asn Gly Phe Gly
1                   5                   10                  15

Phe Lys Asp Ala Val Phe Asp Gly Ser Ser Cys Ile Ser Pro Thr Ile
                20                  25                  30

Val Gln Gln Phe Gly Tyr Gln Arg Arg Ala Ser Asp Asp Gly Lys Leu
            35                  40                  45

Thr Asp Pro Ser Lys Thr Ser Asn Thr Ile Arg Val Phe Leu Pro Asn
    50                  55                  60

Lys Gln Arg Thr Val Val Asn Val Arg Asn Gly Met Ser Leu His Asp
65                  70                  75                  80

Cys Leu Met Lys Ala Leu Lys Val Arg Gly Leu Gln Pro Glu Cys Cys
                85                  90                  95

Ala Val Phe Arg Leu Leu His Glu His Lys Gly Lys Lys Ala Arg Leu
                100                 105                 110

Asp Trp Asn Thr Asp Ala Ala Ser Leu Ile Gly Glu Glu Leu Gln Val
            115                 120                 125

Asp Phe Leu Asp His Val Pro Leu Thr Thr His Asn Phe Ala Arg Lys
    130                 135                 140

Thr Phe Leu Lys Leu
145
```

ACTIVATED RAS INTERACTION ASSAY

Figure 1A:
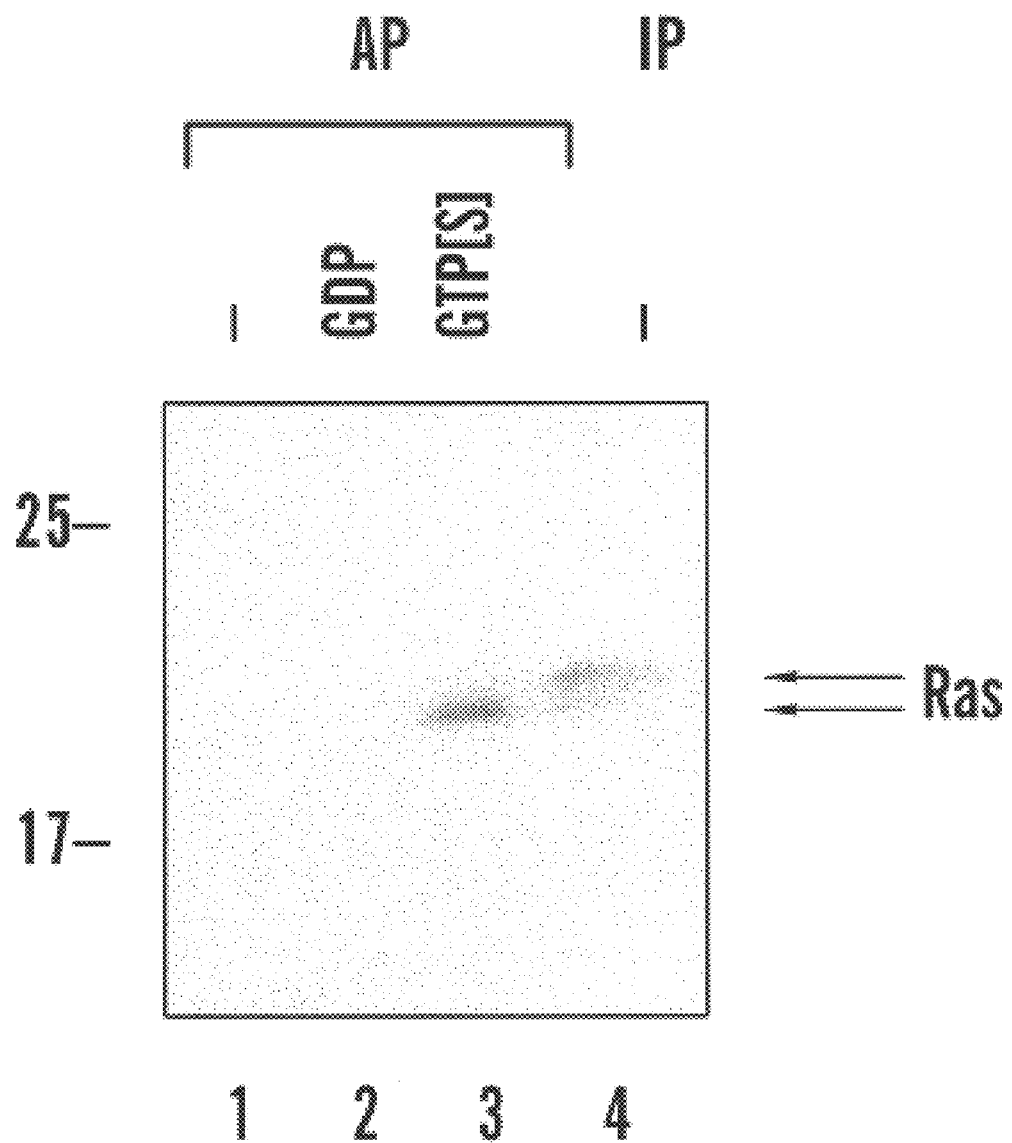

The present application claims the benefit of U.S. Provisional Patent Application Ser. No. 60/030,924, filed Nov. 15, 1996, which is hereby incorporated by reference.

This invention was made with Government support under National Institute of Health Grant No. CA32317. The Government may have certain rights in the invention.

FIELD OF THE INVENTION

The present invention relates to a method for detecting activated ras proteins.

BACKGROUND OF THE INTENTION

Harvey, Kirsten and N ras proteins (termed H-ras, K-ras, and N-ras, respectively) are immunologically related proteins and are collectively termed p21. They are products of the ras family of cellular genes which are found in a wide variety of nucleated mammalian cells. The ras genes appear to be frequent targets of genetic alterations that can lead normal cells along the pathway to malignancy. Ras oncogenes have been identified in a wide array of premalignant and malignant cells.

The p21 proteins consist of about 188–189 amino acids having a molecular weight of about 21,000 daltons. Viral and cellular ras genes encode membrane bound proteins (Willingham et al., *Cell* 19;1005 (1980)) which bind guanine nucleotides (Schlonick et al., *PNAS (USA)* 76:5355 (1979); Papageorge et al., *J. Virol.* 44:509 (1982); and Fine et al., *Cell* 37:151(1984)) and possess intrinsic GTPase activity (McGrath et al., *Nature* 301:644 (1984); Sweet et al., *Nature* 311:273 (1984); Gibbs et al., *PNAS (USA)* 81:5704 (1984); and Manne et al., *PNAS* 82:376 (1985)).

DNA mediated transfection experiments using NIH3T3 cells as recipients have led to the identification of a family of activated transforming genes homologous to the ras genes of the H-ras and K-ras sarcoma viruses. A third member of the ras family designated N-ras has been identified but has not been found to have a retroviral counterpart. Activated (mutated) ras genes are structurally distinct from their normal homologs, having amino acid substitutions in the protein at positions 12, 13, or 61. (Tabin et al., *Nature* 300:143 (1982); Reddy et al., *Nature* 300:149 (1982); Bos et al., *Nature* 315:716 (1985); Yuasa et al., *Nature*, 303:775–779 (1983); Der et al., cell 44:167–176 (Jan. 17, 1986)). Taparowsky et al., *Banbury Report*, 14:123–133 (1983) cited in *Chem. Abstracts* CA 100(1):1425n, teaches that the change at residue 12 from N-terminus of the H ras p21 from glycine to valine is sufficient to convert the normal protein to a transforming protein.

Shimizu et al., *Nature* 304:497–500 (1983) cited in *Chem. Abstracts* 99(19):1530936, teaches the presence of a cysteine residue at amino acid 12 in the human lung cancer cell line calu-1 homolog of the v-Ki-ras gene. Fasano et al., *J. Mol. Appl. Genet.*, 2(2):173–180, cited in *Chem. Abstracts* CA 99(19):153080v, teaches that the T24 H-ras-1 gene product is nearly identical to the v-H-ras p21 transforming protein encoded by Harvey sarcoma virus. Recent reports have shown the presence of activated ras p21 proteins in 40–50% of human colorectal cancers and preneoplastic lesions of the colon termed adenomas (Bos et al., *Nature* 327:293 (1987), Forrester et al., *Nature* 327:299 (1987) and Volgelstein et al., *NEJM* 319:525 (September 1988)). Recent studies have also shown expression of activated ras genes and mutated ras p21 proteins in 20–30% of lung carcinomas (Rodenhuis et al., *Cancer Res.*, 48:5738 (1988)) and over 90% of pancreatic carcinomas (Almoguera et al., *Cell* 53:549 (1988)). In certain forms of leukemia, such as acute myelogeneous leukemia and in certain preleukemic states, activated ras p21 proteins have been described.

These activated ras genes and mutated proteins have also been found in established cell lines as well as primary and metastatic tumors. Gambke et al., *Nature* 307:476, (1984), demonstrated a transforming N-ras gene in bone marrow cells from a patient aith acute myeloblastic leukemia ("AML"). In contrast, DNA from fibroblast cells from the same patient was not transforming.

The p21 ras protein in its normal nonactivated form contains the glycine amino acid at positions 12 and 13 and the glutamine amino acid at position 61. The p21 protein found in normal cells has the following primary amino acid structure for the amino acid sequence 5 to 19: [5]Lysine-leucine-valine-valine-valine-glycine-alanine-glycine-glycine-valine-glycine-lysine-serine-alanine-leucine[19].

Ras proteins act as molecular switches relaying proliferative signals from cell surface receptors to the nucleus and cytoskeleton. Activation of these receptors leads to the activation of a guanines nucleotide exchange factor, which induces the exchange of guanine diphosphate ("GDP") for guanine triphosphate ("GTP"). Specifically, the activation of Ras by the binding of GTP is required for the ability of many growth factors and cytokines to induce non-proliferating cells to enter G1 phase of the cell cycle. Activation of membrane-bound Ras by growth factor and cytokine receptors is generally achieved by the recruitment of Grb2-Sos complexes to the receptors themselves or to adaptor proteins such as Shc.

A primary target of activated Ras during growth factor stimulation is Raf, which is the first component of a protein kinase cascade that leads to activation of the MAP kinases Erk1 and Erk2 (Avruch et al., "Raf Meets Ras: Completing the Framework of a Signal Transduction Pathway," *Trends Biochem. Sci.*, 19:279–83 (1994)). The phosphorylation of transcription factors by these MAP kinases results in the expression of immediate early response genes, such as c-fos, that are required for early G1 progression. Although these signalling events occur within minutes of growth factor stimulation, microinjection of neutralizing anti-Ras antibodies in late G1 phase blocks progression of fibroblasts into S phase (Mulcahy, et al., "Requirement for Ras Protooncogene Function During Serum-Stimulated Growth of NIH 3T3 Cells, *Nature*, 313:214–43 (1985)). Furthermore, studies using combinations of cell cycle inhibitors and anti-Ras microinjection clearly demonstrate multiple points of Ras requirement in early and late G1 phase (Dobrowolski et al., "Cellular Ras Activity Is Required for Passage Through Multiple Points of the G-0-G-1 Phase in BALB-c 3T3 Cells," *Molecular and Cellular Biology*, 14:5441–49 (1994). These findings, together with the observations that expression of oncogenic Ras increases cyclin D1 levels and shortens G1 phase (Liu, et al., "Ras Transformation Results in an Elevated Level of Cyclin D1 and Acceleration of G1 Progression in NIH 3T3 Cells," *Mol. Cell Biol.*, 15:3654–63 (1995); Winston et al., "Regulation of the Cell Cycle Machinery by Oncogenic Ras," *Oncogene*, 12:127–34 (1996)) and that Ras and cyclin D1 cooperate in cellular transformation assays (Hinds et al., "Function of a Human Cyclin Gene as an Oncogene," *Proc. Natl. Sci. USA*, 91:709–13 (1994); Lovec et al., "Oncogenic Activity Cyclin D1 Revealed Through Cooperation with Ha-ras; Link Between Cell Cycle Control and Malignant Transformation," *Oncocene*, 9:323–26 (1994)) point to an important role for Ras in regulating progression from G1 into S phase.

However, important questions remain as to whether Ras controls signalling everts during cell cycle progression, and, if so, at which point in the cell cycle it is activated. The Ras proteins function by cycling between active and inactive forms; in the active form Ras binds to GTP and is converted to the inactive form by conversion of GTP to GDP. Activation of Ras is promoted by numerous extracellular signals such as growth factors, and, when activated, Ras specifically interacts with intracellular targets to transduce growth stimulatory signals from the cell's exterior to the nucleus. One such target of activated Ras in the Raf-1 proto-oncoprotein, a protein kinase involved in signalling to the nucleus.

The mutations of ras gene., that occur in human cancer, as discussed above, cause a constitutive activation of the Ras protein, and the resulting deregulation of growth control is believed to contribute to the cancer process. Furthermore, it is known that ras gene mutation occurs at a particular: stage in the multi-step process of colon cancer progression, and it is likely that ras mutations might occur at defined, perhaps early, stages in other types of cancer. Accordingly, the detection of ras activation in human tumors might be of great diagnostic and prognostic use.

Most previous analyses of Ras activation have measured the GTP:GDP ratio of immunoprecipitated Ras following [32P] radiolabelling of cells (Gibbs et al., "Modulation Of Guanine Nucleotides Bound to Ras in Nih3t3 Cells by Oncogenes Growth Factors and the Gtpase Activating Protein Gap," *J. Biol. Chem.*, 265:20 437–42 (1990); Satoh, et al., "Platelet-Derived Growth Factor Stimulates Formation of Active p21ras-GTP Complex in Swiss Mouse 3T3 Cells," *Proc. Natl. Acad. Sci. USA*, 87:59 93–97 (1990); Gibbs, J. B., "Determination of Guanine Nucleotides Bound to Ras in Mammalian Cells," *Methods Enzymol.*, 255:118–25 (1995); Satoh, et al., "Measurement of Ras-Bound Guanine Nucleotides in Stimulated Hematopoietic Cells," *Methods Enzymol.*, 255:149–55 (1995). The ability of even very low levels of radioisotopes to cause rapid (i.e., within a few hours) cell cycle arrest or apoptosis (Wimber D. E., "Effects of Intracellular Irradiation with Tritium," *Adv. Radiat. Biol.*, 1:85–115 (1964); Dover et al., "p53 Expression in Cultured Cells Following Radioisotope Labelling," *J. Cell Sci.*, 107:1181–84 (1994); Yeargin, et al., "Elevated Levels of Wild-Type p53 Induced by Radiolabelling of Cells Leads to Apoptosis or Sustained Growth Arrest," *Current Biology*, 5:423–31 (1995), however, precludes the use of such assays to measure Ras activity in cycling cells.

Previous assays of activated Ras, such as U.S. Pat. No. 5,443,956 to Carney, have employed antibodies specific for particular activated Ras mutants. This type of assay suffers the drawbacks of not detecting all potential activating mutations and rot detecting Ras activation in response to activation of other oncogenes.

Chuang et al., "Critical Binding and Regulating Interactions Between Ras and Raf Occur Through a Small, Stable N-Terminal Domain of Raf and Specific Ras Effector Residues," *Molecular & Cellular Biology*, 14(8):5318–325 (1994); Warne et al., "Direct Interaction of Ras and the Amino-terminal Region of Raf-1 in vitro, *Nature*, 364:352–355 (1993); and Ghosh et al., "The Cysteine-rich Region of Raf-1 Kinase Contains Zinc, Translocates to Liposomes, and Is Adjacent to a Segment That Binds GTP-Ras," *J. Biological Chem.*, 269(13):10000–10007 (1994) study the interaction of the GTP-bound activated ras protein to an raf-1-GST fusion protein using purified recombinantly produced GTP-ras. Thus, these references did not study reactions using lysates from cell cultures, such as cells taken from cancerous tissue. One would have expected that the many proteins and other components present in a lysate would interfere with the binding of GTP-ras to raf-1. Furthermore these references studied Ras-Raf interaction under optimized conditions, for instance maximized GTP "loading" of Ras and, therefore, were unable to study the effects of complex cellular regulatory networks on Ras activation. These references also employed recombinant sources of Ras which, therefore, were not subject to the post-translational modifications of Ras that occur in mammalian cells.

The present invention is directed to overcoming these deficiencies.

SUMMARY OF THE INVENTION

The present invention relates to a method for detecting activated ras protein which includes immobilizing a protein on a solid support, incubating the immobilized protein with lysates from cultured cells where the lysates include activated ras protein, and determining the amount of activated ras protein bound to the immobilized protein.

Another aspect of the present invention relates to a method of detecting ras oncogenic related malignancy in a human subject. The method includes collecting a cell culture from the human subject, providing lysates from the cell culture, incubating the lysates with an immobilized protein, and determining the amount of activated ras protein bound to the immobilized protein.

The present method has numerous advantages over previously disclosed methods. First, this method may be used to measure activation levels in whole tissue samples since the assay does not require pre-treatment of samples with radioactive isotopes, as required in previously described assays. Second, this assay enables detection of activation of specific ras family members. This is accomplished by probing the bound proteins with antibodies specific to either K ras, H ras, N ras, or all three. Therefore, it is possible to detect the specific ras isozymes. Third, this method can be used to measure the activation of the ras oncogene as an indication of human cancer. Mutations in the ras family are present in many human cancers. The mutations of ras genes that occur in human cancer cause a constitutive activation of the ras protein. Therefore, the disclosed method may be used for diagnostic and prognostic use. In addition, this assay provides an advantage over previously disclosed assays for diagnosis of cancer. The present method detects all means of activation of the ras protein. In contrast, previously disclosed assays have employed antibodies specific for particular activated ras mutants and therefore are unable to detect all potential activating mutations or ras activation in response to activation of other oncogenes. Further, the present invention teaches that detection of activated ras protein can be accomplished in lysates from cell cultures, i.e. cells taken directly from cancerous tissue, whereas previous reports had only shown that activated GTP-bound ras binds to raf-1 when expressed as a fusion protein using purified recombinantly produced raf-1 and ras protein. Finally, the method of the subject invention can also be used to study the normal regulation of ras proteins by detecting activated ras.

DETAILED FIGURES OF THE INVENTION

FIGS. 1(*a*), 1(*b*), and 1(*c*) illustrate an assay for activated Ras.

FIGS. 2(*a*), 2(*b*), and 2(*c*) illustrate activation of Ras during G1 phase in HeLa cells.

FIGS. 3(*a*) and 3(*b*) illustrate relative activation of Ras and Erk kinases in G1 phase in HeLa cells.

Figure 4A:
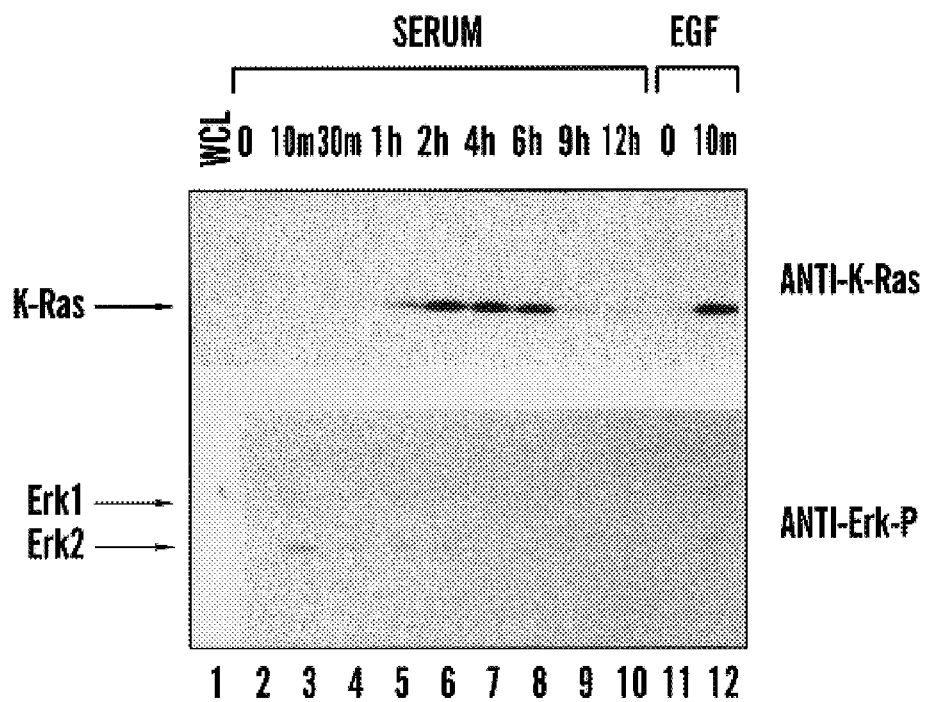
Figure 4B:
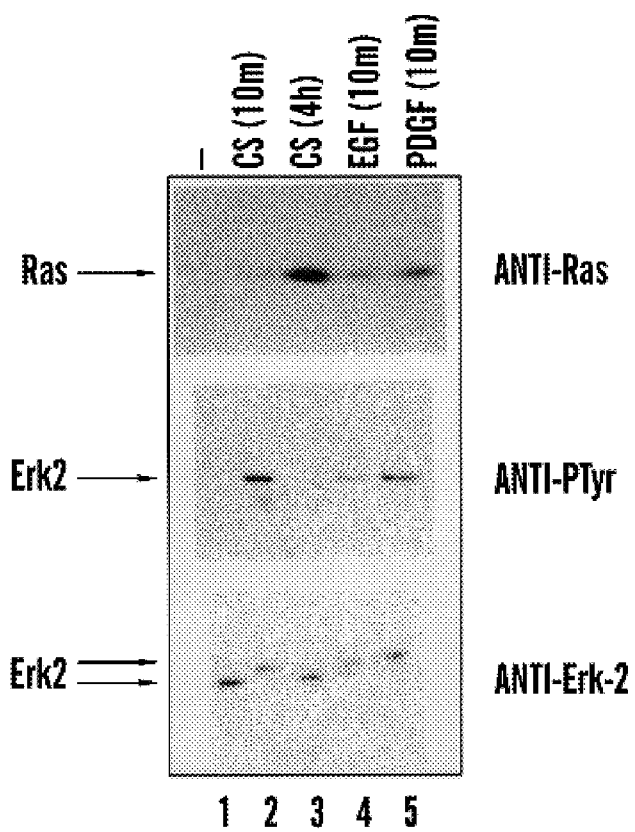

FIGS. 4(a) and 4(b) illustrate relative activation of Ras and Erk kinases in G1 phase in NIH 3T3 cells.

DETAILED DESCRIPTION OF THE INVENTION

The present invention relates to a method for detecting activated ras protein. The method includes immobilizing a protein on a solid support, incubating the immobilized protein with lysates from cultured cells, where the lysates include activated ras protein, and determining the amount of activated ras protein bound to the immobilized protein.

Another aspect of the present invention relates to a method of detecting ras oncogenic related malignancy in a human subject. The method includes collecting a cell culture from the human subject, providing lysates from the cell culture, incubating the lysates with an immobilized protein, and determining the amount of activated ras proteins bound to the immobilized protein.

The present invention detects activated ras proteins, whether the activation is caused by mutation of the ras genes, by the action of other oncogenes, or due to other factors.

The assay is based on the principle that activated Ras binds specifically to various proteins. Accordingly, a protein immobilized on a solid support is used to bind the activated ras protein. Suitable proteins include phosphatidylinositol-3 kinase (Rodriguez-Viciana et al., *Nature*, 370:527–532 (1994), which is hereby incorporated by reference) the Ral guanine nucleotide exchange factors RalGDS (Spaargaren et al., *Proc. Natl. Acad. Sci. USA*, 91:12609–12613 (1994), which is hereby incorporated by reference), Rgl (Kikuchi et al. *Mol. Cell. Biol.*, 14:7483–7491 (1994), which is hereby incorporated by reference) and Rlf (Wolthuis et al. *Oncogene*, 13:353–362 (1996), which is hereby incorporated by reference), the GTPase activating proteins p12-RasGAP and neurofibromin, Rin (Ilan et al., *Mol. Cell. Biol.*, 15:1318–1323 (1995), which is hereby incorporated by reference) and several other Ras-binding proteins (Ponting et al., *Trends Biochem. Sci.*, 21:423–425 (1996), which is hereby incorporated by reference).

Preferably, the protein is a raf-1 protein. Raf-1 comprises an amino acid protein sequence corresponding to SEQ. ID. No. 1 as follows:

```
Met Glu His Ile Gln Gly Ala Trp Lys Thr Ile Ser Asn Gly Phe Gly
1               5                   10                  15

Phe Lys Asp Ala Val Phe Asp Gly Ser Ser Cys Ile Ser Pro Thr Ile
            20                  25                  30

Val Gln Gln Phe Gly Tyr Gln Arg Arg Ala Ser Asp Asp Gly Lys Leu
        35                  40                  45

Thr Asp Pro Ser Lys Thr Ser Asn Thr Ile Arg Val Phe Leu Pro Asn
    50                  55                  60

Lys Gln Arg Thr Val Val Asn Val Arg Asn Gly Met Ser Leu His Asp
65                  70                  75                  80

Cys Leu Met Lys Ala Leu Lys Val Arg Gly Leu Gln Pro Glu Cys Cys
                85                  90                  95

Ala Val Phe Arg Leu Leu His Glu His Lys Gly Lys Lys Ala Arg Leu
                100                 105                 110

Asp Trp Asn Thr Asp Ala Ala Ser Leu Ile Gly Glu Glu Leu Gln Val
            115                 120                 125

Asp Phe Leu Asp His Val Pro Leu Thr Thr His Asn Phe Ala Arg Lys
        130                 135                 140

Thr Phe Leu Lys Leu Ala Phe Cys Asp Ile Cys Gln Lys Phe Leu Leu
145                 150                 155                 160

Asn Gly Phe Arg Cys Gln Thr Cys Gly Tyr Lys Phe His Glu His Cys
                165                 170                 175

Ser Thr Lys Val Pro Thr Met Cys Val Asp Trp Ser Asn Ile Arg Gln
            180                 185                 190

Leu Leu Leu Phe Pro Asn Ser Thr Ile Gly Asp Ser Gly Val Pro Ala
        195                 200                 205

Leu Pro Ser Leu Thr Met Arg Arg Met Arg Glu Ser Val Ser Arg Met
    210                 215                 220

Pro Val Ser Ser Gln His Arg Tyr Ser Thr Pro His Ala Phe Thr Phe
225                 230                 235                 240

Asn Thr Ser Ser Pro Ser Ser Glu Gly Ser Leu Ser Gln Arg Gln Arg
                245                 250                 255

Ser Thr Ser Thr Pro Asn Val His Met Val Ser Thr Thr Leu Pro Val
            260                 265                 270
```

-continued

```
Asp Ser Arg Met Ile Glu Asp Ala Ile Arg Ser His Ser Glu Ser Ala
        275                 280                 285

Ser Pro Ser Ala Leu Ser Ser Ser Pro Asn Asn Leu Ser Pro Thr Gly
        290                 295                 300

Trp Ser Gln Pro Lys Thr Pro Val Pro Ala Glu Arg Glu Arg Ala Pro
305                 310                 315                 320

Val Ser Gly Thr Gln Glu Lys Asn Lys Ile Arg Pro Arg Gly Gln Arg
                325                 330                 335

Asp Ser Ser Tyr Tyr Trp Glu Ile Glu Ala Ser Glu Val Met Leu Ser
                340                 345                 350

Thr Arg Ile Gly Ser Gly Ser Phe Gly Thr Val Tyr Lys Gly Lys Trp
        355                 360                 365

His Gly Asp Val Ala Val Lys Ile Leu Lys Val Val Asp Pro Thr Pro
        370                 375                 380

Glu Gln Phe Gln Ala Phe Arg Asn Glu Val Ala Val Leu Arg Lys Thr
385                 390                 395                 400

Arg His Val Asn Ile Leu Leu Phe Met Gly Tyr Met Thr Lys Asp Asn
                405                 410                 415

Leu Ala Ile Val Thr Gln Trp Cys Glu Gly Ser Ser Leu Tyr Lys His
                420                 425                 430

Leu His Val Gln Glu Thr Lys Phe Gln Met Phe Gln Leu Ile Asp Ile
        435                 440                 445

Ala Arg Gln Thr Ala Gln Gly Met Asp Tyr Leu His Ala Lys Asn Ile
        450                 455                 460

Ile His Arg Asp Met Lys Ser Asn Asn Ile Phe Leu His Glu Gly Leu
465                 470                 475                 480

Thr Val Lys Ile Gly Asp Phe Gly Leu Ala Thr Val Lys Ser Arg Trp
                485                 490                 495

Ser Gly Ser Gln Gln Val Glu Gln Pro Thr Gly Ser Val Leu Trp Met
                500                 505                 510

Ala Pro Glu Val Ile Arg Met Gln Asp Asn Asn Pro Phe Ser Phe Gln
        515                 520                 525

Ser Asp Val Tyr Ser Tyr Gly Ile Val Leu Tyr Glu Leu Met Thr Gly
        530                 535                 540

Glu Leu Pro Tyr Ser His Ile Asn Asn Arg Asp Gln Ile Ile Phe Met
545                 550                 555                 560

Val Gly Arg Gly Tyr Ala Ser Pro Asp Leu Ser Lys Leu Tyr Lys Asn
                565                 570                 575

Cys Pro Lys Ala Met Lys Arg Leu Val Ala Asp Cys Val Lys Lys Val
                580                 585                 590

Lys Glu Glu Arg Pro Leu Phe Pro Gln Ile Leu Ser Ser Ile Glu Leu
        595                 600                 605

Leu Gln His Ser Leu Pro Lys Ile Asn Arg Ser Ala Ser Glu Pro Ser
        610                 615                 620

Leu His Arg Ala Ala His Thr Glu Asp Ile Asn Ala Cys Thr Leu Thr
625                 630                 635                 640

Thr Ser Pro Arg Leu Pro Val Phe
                645
```

More preferably, the protein used to bind the activated ras protein is a region of the Raf-1 protein kinase, as described in Warne et al., "Direct Ineraction of Ras and the Amino-terminal region of Raf-1 in vitro," *Nature*, 364:353–55 (1993)("Warne"); Chuang et al., "Critical Binding and Regulatory Interactions between Ras and Raf Occur Through a Small, Stable N-Terminal Domain of Raf and Specific Ras Effector Residues," *Molecular & Cellular Bio.*, 14(8); 5318–325(1994) (Chuang"); Ghosh et al., "The Cysteine-rich Region of Raf-1 Kinase Contains Zinc, Translocates to Liposomes, and Is Adjacent to a Segment That Binds GTP-Ras," *J. Bio. Chem.*, 269(13):10000–10007

(1994)("Ghosh"), Pumiglia et al., "Raf-1 N-Terminal Sequences Necessary for Ras-Raf Interaction and Signal Transduction," *Mol. Cell. Biol.*, 15:398–406 (1995); Herrmann et al., "Quantitative Analysis of the Complex Between p21ras and the Ras-Binding Domain of the Human Raf-1 Protein Kinase," *J. Biol. Chem.*, 270:2901–05 (1995) ("Herrmann"); and Nassar et al., "The 2.2 A Crystal Structure of the Ras-Binding Domain of Serine-Threonine Kinase c-Raf1 in Complex with Rap1A and a GTP Analogue," *Nature*, 375:554–60 (1995), which are hereby incorporated by reference. Typically, amino acids 51–131 (Herrmann), amino acids 1–257 (Warne; U.S. Pat. No. 5,582,995 to Avruch et al., which is hereby incorporated by reference), amino acids 1–147 (Ghosh) or amino acids 1–149 of Raf1 binds to activated ras protein. These regions of the Raf-1 protein kinase are known as the Ras binding domain ("RBD"). However, any region of c-Raf-1, A-Raf, or B-Raf containing the minimal Ras binding domain could be used as a specific probe for activated ras, as could the ras binding regions of other ras effector molecules such as phosphoinositide 3-kinase. The level of success achieved using a particular RBD depends on the affinity of the activated ras-RBD interaction, the specificity for binding GTP-Ras versus GDP-Ras, and the ability to produce intact, functional recombinant RBD. Preferably, the present invention utilizes a protein comprising an amino acid sequence corresponding to SEQ. ID. No. 2 as follows:

be transformed into a suitable expression system, such as, for example, *E. coli* XA90, DH5alpha, JM101, or JM109, in which the expression of the GST fusion protein can be induced with isopropyl-beta-D-thiogalactopyranoside ("IPTG").

After transformation of the resulting construct into a suitable expression system, induction with IPTG should yield the fusion protein as a major constituent of soluble, cellular proteins. The fusion proteins can be purified by methods known to those skilled in the art, including purification by glutathione affinity chromatography. The purity of the product can be assayed by methods known to those skilled in the art, such gel electrophoresis.

Most preferably, a prokaryotic expression plasmid derived from human Raf-1 cDNA sequences and plasmid pGEX-2T is utilized to produce the fusion protein GST-RBD. In particular, plasmid pGEX-RBD is used to produce the fusion protein GST-RBD in *E. coli* which is purified, typically, by affinity chromatography with glutathione Sepharose.

The solid support may be beads, a microtiter plate, or other known supports. Preferably, the solid support is glutathione Separose beads.

Next, the immobilized protein is incubated with lysates of cultured cells, which include activated ras proteins. Preferably, the cultured cells are taken from human subjects and lysed. Typically, lysing involves cell lysis and extraction

```
Met Glu His Ile Gln Gly Ala Trp Lys Thr Ile Ser Asn Gly Phe Gly
1             5                   10                  15

Phe Lys Asp Ala Val Phe Asp Gly Ser Ser Cys Ile Ser Pro Thr Ile
            20                  25                  30

Val Gln Gln Phe Gly Tyr Gln Arg Arg Ala Ser Asp Asp Gly Lys Leu
        35                  40                  45

Thr Asp Pro Ser Lys Thr Ser Asn Thr Ile Arg Val Phe Leu Pro Asn
    50                  55                      60

Lys Gln Arg Thr Val Val Asn Val Arg Asn Gly Met Ser Leu His Asp
65                  70                  75                  80

Cys Leu Met Lys Ala Leu Lys Val Arg Gly Leu Gln Pro Glu Cys Cys
                85                  90                  95

Ala Val Phe Arg Leu Leu His Glu His Lys Gly Lys Lys Ala Arg Leu
                100                 105                 110

Asp Trp Asn Thr Asp Ala Ala Ser Leu Ile Gly Glu Glu Leu Gln Val
            115                 120                 125

Asp Phe Leu Asp His Val Pro Leu Thr Thr His Asn Phe Ala Arg Lys
        130                 135                 140

Thr Phe Leu Lys Leu Ala Phe Cys Asp Ile Cys Gln Lys Phe Leu Leu
145
```

Preferably, the protein utilized in the present invention includes the ras binding domain as a fusion protein. Preferably, the fusion protein includes glutathione-S-transferase ("GST"), and is identified as GST-RBD. In addition to GST other affinity purification "tags" such as hexa-histidine or antibody-directed epitope tags can be fused to the RBD and used for purification and detection.

The fusion proteins are produced by standard techniques. For example, a chimeric gene encoding a GST fusion protein can be constructed by fusing DNA encoding a polypeptide or polypeptide fragment to the DNA encoding the carboxyl terminus of GST (Smith et al., *Gene*, 67:31 (1988), which is hereby incorporated by reference). The fusion construct, can of cellular proteins with nonionic detergents. Thus, the activated ras proteins present in the lysates bind specifically to the protein. Typically, any activated ras proteins present in the lysates will bind specifically to the RBD present in the raf-1 portion of the fusion protein. Typically, the lysates are then washed to remove unbound proteins. Bound activated ras proteins are eluted and the amount of Ras protein, typically found as GTP-bound activated Ras, is determined. Typically, the amount of ras protein is determined by sodium dodecyl sulfate-polyacrylamide gel electrophoresis ("SDS-PAGE"), Western blotting, and probing.

Typically, probing occurs by contacting the activated ras proteins with antibodies, binding portions thereof, probes, or ligands. Preferably, probing occurs utilizing anti-ras antibodies, such as anti-pan Ras, anti-K-Ras, or anti-H-Ras, or anti-N-Ras, or binding portions thereof. Such binding portions thereof include Fab fragments, F[ab']2 fragments, and Fv fragments. These antibody fragments can be made by conventional procedures, such as proteolytic fragmentation procedures, as described in Goding, Monoclonal Antibodies: Principles and Practice, pp. 98–118 (N.Y. Academic Press 1983), which is hereby incorporated by reference.

Alternatively, the present invention can utilize probes or ligands found either in nature or prepared synthetically by recombinant DNA procedures or other biological or molecular procedures. Suitable probes or ligands are those which bind to the activated ras proteins. Such probes or ligands can be, for example, proteins, peptides, lectins, or nucleic acid probes.

The antibodies or probes may be labeled to be detected by typical methods. Alternatively, the antibodies are contacted with a second labeled antibody, such as a mouse or rabbit antibody, which is suitable for detecting all mouse or rabbit antibodies. The labeled anti-mouse or anti-rat antibody is then detected by standard techniques, such as electrochemiluminescence.

Examples of labels useful for detecting in the present invention are radiolabels such as $^{131}I$, $^{111}In$, $^{123}I$, $^{99m}Tc$, $^{32}P$, $^{125}I$, $^{3}H$, $^{14}C$, and $^{188}Rh$, fluorescent labels such as fluorescein and rhodamine, nuclear magnetic resonance active labels, positron emitting isotopes detectable by a positron emission tomography ("PET") scanner, chemiluminescers such as luciferin, and enzymatic markers such as peroxidase or phosphatase. The antibodies can be labeled with such reagents using techniques known in the art. For example, see Wensel and Meares, *Radioimmunoimaging and Radioimmunotherapy*, Elsevier, New York (1983), which is hereby incorporated by reference, for techniques relating to the radiolabeling of antibodies. See also, D. Colcher et: al., "Use of Monoclonal Antibodies as Radiopharmaceuticals for the Localization of Human Carcinoma Xenografts in Athymic Mice", *Meth. Enzymol.* 121: 802–816 (1986), which is hereby incorporated by reference.

This method is useful to determine the presence of activated ras proteins associated with human cancers, such, for example, colon cancer, breast cancer, lung carcinomas, pancreatic carcinomas, and certain forms of leukemias.

This method can be used to confirm the activation of Ras proteins following epidermal growth factor treatment of mouse NIH 3T3 cells and human HeLa cells. Further, the assay can be used to analyze the level of activation of Ras proteins in cell or tissue extracts. Since the assay does not require pre-treatment of samples with radioactive isotopes, as is required in previously described assays, it can be conveniently used to measure Ras activation levels in whole tissue samples. The assay also enables detection of activation of specific Ras family members, using isotope-specific antibodies. The ease and convenience of the assay also renders it suitable for evaluating the potential of drugs and suspected or known bio-active compounds in the activation of Ras proteins in cultured cells.

Using the assay of the present invention, it was determined that Ras was activated in HeLa cells following release from mitosis and in NIH 3T3 fibroblasts following serum-stimulated cell cycle entry. In each case, however, peak Ras activation occurred in mid-G1 phase. Ras activation in HeLa cells at mid-G1 phase was dependent on RNA and protein synthesis and was not associated with tyrosine phosphorylation of Shc proteins and their binding to Grb2. Significantly, activation of Ras and the Erk sub-group of MAP kinases were not temporally correlated during G1 phase progression.

Activation of Ras in mid-G1 phase appears to differ in many respects to its rapid activation by growth factors suggesting a novel mechanism of regulation, possibly intrinsic to cell cycle progression. Furthermore, the temporal dissociation between Ras activation and Erk activation suggests that Ras targets alternate effector pathways during G1 phase progression.

EXAMPLES

Materials and Methods

Cell culture and synchrony

HeLa S3 cells and NIH 3T3 fibroblasts were grown in Dulbecco's minimal essential medium ("DMEM") containing 10% calf serum. HeLa cells were arrested in mitosis by means of a thymidine-nocodazole double block. HeLa cells growing in DMEM plus 10% calf serum were incubated in 2 mM thymidine for 20–24 hours, washed with DMEM, trypsinized and replated. Nocodazole (0.1 µg/ml) was added 2 hours later and mitotic cells were collected by shake-off 12–14 hours later. For mitotic release, the cells were washed twice with DMEM, resuspended in DMEM/10% serum and incubated in suspension in spinner culture (HeLa cells grow synchronously in suspension (Heintz, et al., "Regulation of Human Histone Gene Expression; Kinetics of Accumulation and Changes in the Rate of Synthesis and in the Half-Lives of Individual Histone mRNAs During HeLa Cell Cycle," *Mol. Cell. Biol.*, 3:539–50 (1983), which is hereby incorporated by reference) or allowed to re-attach to plates (in FIG. 2b, lanes 5–12). HeLa and NIH 3T3 cells were incubated in DMEM without serum for 24 hours before treatment with growth factors or serum.

Cell lysis, immunoprecipitations and kinase assays

Suspension and adherent cells were washed twice with ice-cold Hepes-buffered saline ("HBS"). In FIG. 1a, cells were lysed in 20 mM N-(2-hydroxy ethyl) piperazine-N'-(2-ethane sulfonic acid) ("HEPES"), pH 7.5, 150 mM NaCl, 5 mM ethylenediaminetetraacetic acid ("EDTA"), 1% NP-40 (a nonionic detergent by Calbiochem, San Diego, Calif.), 10 µg/ml leupeptin, 10 µg/ml aprotinin, and the lysates were dialysed extensively against the same buffer without protease inhibitors. After clearing by centrifugation, dialysed lysates (0.3 ml) were incubated with or without 1 mM guanosine diphosphate ("GDP") or 0.5 mM Guanosine 5'-O-(3-thiotriphosphate) ("GTPγS") for 10 minutes and then with 10 mM MgCl$_2$ for 60 minutes at room temperature. For affinity and immuno-precipitations in other Figures, cells were lysed in Mg2+-containing lysis buffer (25 mM HEPES, pH 7.5, 150 mM NaCl, 1% NP-40, 0.25% Na deoxycholate, 10% glycerol, 25 mM NaF, 10 mM MgCl$_2$, 1 mM EDTA, 1 mM Na vanadate, 10µ µg/ml leupeptin, 10 µg/ml aprotinin) at 0.4–0.8 ml/plate. Lysates were either used immediately or frozen in liquid N$_2$ and stored at −70° C. until use. In FIG. 1, equal volumes of lysate (0.3 ml for affinity; 0.15 ml for immuno) were used for precipitations. In other Figures, protein concentrations of lysates were determined and equal amounts of proteins were used. For immunoprecipatation, lysates were incubated with 1 µg anti-Ras monoclonal 238 (Santa Cruz, Santa Cruz, Calif.) for 60 minutes and then with protein G Sepharose (20 µl packed beads) for 40 minutes. Immunoprecipatation of Shc proteins was with 1 µg anti-Shc polyclonal antibody (Transduction Labs, Lexington, Ky.) for 4 hours followed by collection on protein A Sepharose beads. Immunoprecipatation of Erk2 was with 0.5 µg anti-Erk R2 polyclonal (UBI, Lake Placid, N.Y.) plus 0.5 µg anti-Erk2 (sc-154; Santa Cruz, Santa Cruz, Calif.) for 4 hours followed by collection on protein A Sepharose beads. Although these antibodies recognize Erks 1 and 2, only Erk2 was detected in immunoprecipitates. All precipitates were washed 3 times with lysis buffer containing 10 mM $MgCl_2$ and bound proteins were eluted with SDS-PAGE sample buffer. For anti-Shc immunoprecipitates proteins were eluted in SDS-PAGE sample buffer containing 20 mM N-ethyl maleimide (to prevent IgG reduction and interference of heavy and light chains on blots). Proteins were resolved on 10% or 11% acrylamide gels and Western blotted. Blots were probed with anti-pan Ras (Transduction Labs, Lexington, Ky.), anti-K-Ras (sc-30) or anti-H-Ras (sc-29) monoclonal antibodies (Santa Cruz, Santa Cruz, Calif.), anti-Shc or anti-Gib2 monoclonal antibodies (Transduction Labs, Lexington, K.Y.), anti-PTyr monoclonal 4G10 (UBI, Lake Placid, N.Y.), anti-Erk2 monoclonal antibody (Transduction Labs, Lexington, Ky.) or anti-phospho-MAP kinase polyclonal antibody (New England Biolabs, Beverly, Mass.) detected with anti-mouse or anti-rabbit peroxidase and visualized by an electrochemiluminescence ("ECL") detection system (NEN, Boston, Mass.).

In-gel kinase assays were performed on 10% acrylamide mini-gels with myelin basic protein (0.4 mg/ml) polymerized into them, essentially as described previously (Kameshita, et al., "A Sensitive Method for Detection of Calmodulin-Dependent Protein Kinase II Activity in Sodium Dodecyl Sulfate-Polyacrylamide Gel," Anal. Biochem., 183:139–43 (1989) and Hibi, et al., "Identification of a Oncoprotein- and UV-Responsive Protein Kinase That Binds and Potentiates the c-Jun Activation Domain," Genes Devel., 7:2135–48 (1993), which are hereby incorporated by reference). The kinase reaction was carried out in 10 ml of 50 mM Tris-Cl, pH 7.5, 0.1% NP-40, 1 mM DTT, 20 µM [$\gamma$-$^{32}$P] adenosine triphosphate ("ATP")(~2.5 mCi/µmol for 40 minutes.

Example 1

Assay for detection of activated Ras

To create an expression vector for production of GST-RBD, a BamHI-HinDIII fragment of plasmid pKScRaf1 was blunt-ended and ligated into the SmaI site of pGEX-2T. pGEX-RBD encodes amino acids 1–149 of cRaf-1 fused to GST. Plasmid pGEX-RBD has been deposited pursuant to, and in satisfaction of, the requirements of the Budapest Treaty on the International Recognition of the Deposit of Microorganisms for the Purposes of Patent Procedure with the American Type Culture Collection ("A.T.C.C.") at 10801 University Boulevard, Manassas, Va. 20110–2209. Plasmid pGEX-RBD was deposited on Sept. 21, 1999, and received A.T.C.C. Designation Number PTA-738. GST-RBD expression in transformed E. coli was induced with 1 mM isopropyl-beta-D-thiogalacto pyranoside ("IPTG") for 1–2 hours and the fusion protein was purified on glutathione Sepharose beads. The beads were washed in 20 mM HEPES, pH 7.5, 120 mM NaCl, 10% glycerol, 0.5% NP-40, 2 mM EDTA, 10 µg/ml leupeptin, 10 µg/ml aprotinin, stored in the same buffer at 4° C., and used within 2–3 days of preparation.

Dialyzed detergent lysates of HeLa cells were treated with or without guanine nucleiotides and then incubated with the GST-RBD fusion protein immobilized on beads. For affinity precipitation, lysates were incubated with GST-RBD pre-bound to glutathione Sepharose (~15 µl packed beads, ~15–30 µg protein) for 30 minutes at 4° C. with rocking. Bound proteins were eluted with SDS-PAGE sample buffer, resolved on 11% acrylamide gels and Western blotted. Blots were probed with anti-pan Ras (Transduction Labs, CITY, STATE), anti-K-Ras (sc-30) or anti-H-Ras (sc-29) monoclonal antibodies (Santa Cruz, CITY, STATE).

Figure 1B:
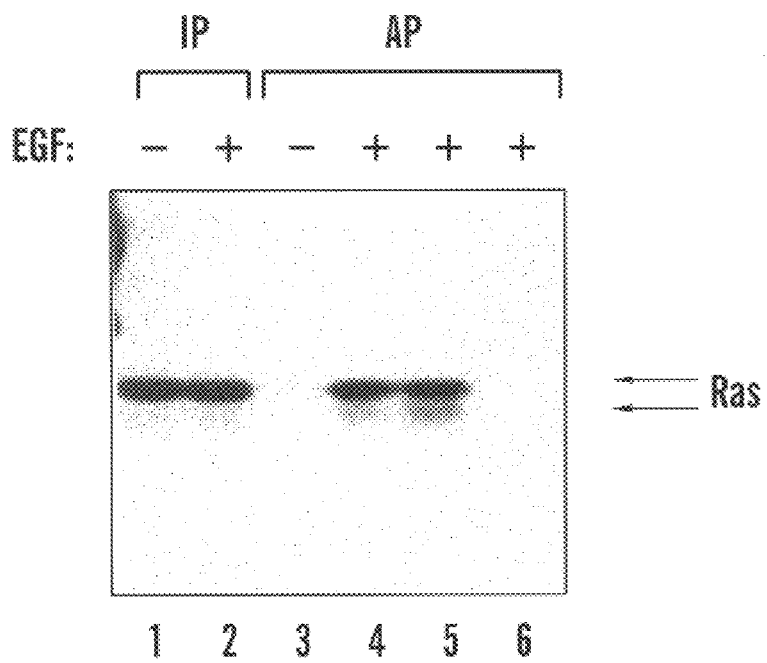
Figure 1C:
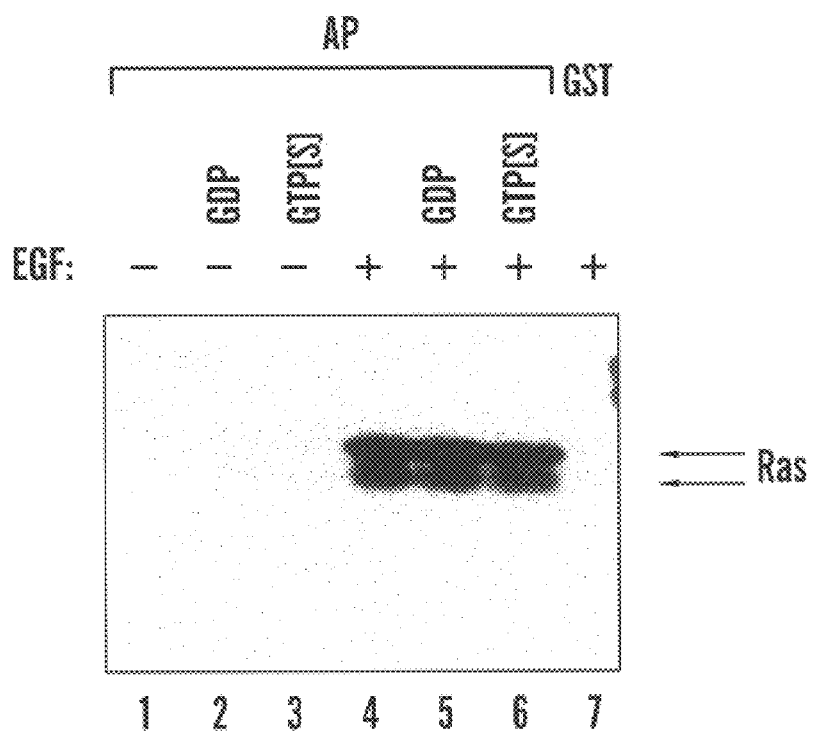

The results are shown in FIGS. 1(a)–(c). In FIG. 1(a), the dialysed HeLa cell Lysates were incubated without (lane 1,4) or with GDP (lane 2) or with GTPS (lane 3). Lanes 1–3 show the GST-RBD affinity precipitates from lysates and lane 4 shows anti-Ras immunoprecipitate. Ras was affinity precipitated by GST-RBD in the GTPS-bound, but not the GDP-bound or nucleotide-free form (FIG. 1a, lanes 1–3). Therefore, although Raf-RBD can bind Ras-GDP with a significantly lower affinity than Ras-GTP, under the conditions of this assay, only Ras-GTP is detected.

Figure 2A:
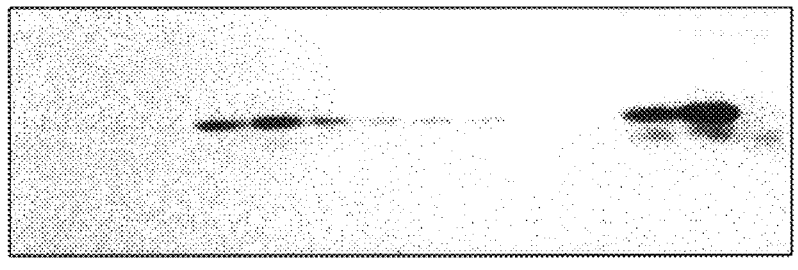
Figure 2B:
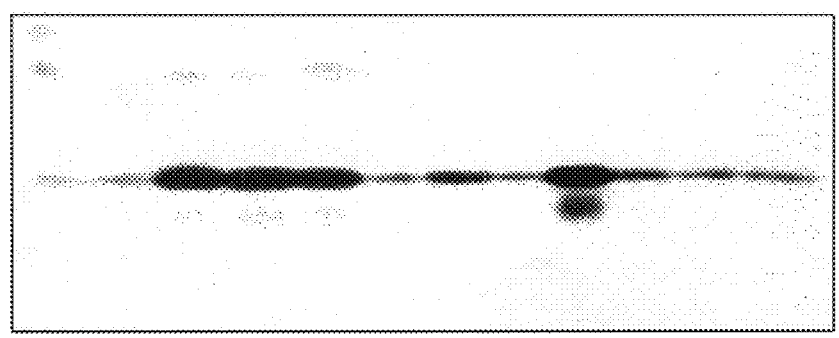

In FIG. 2(b), serum-starved HeLa cells were treated with (lanes 2,4–6) or without (lanes 1,3) 200 ng/ml epidermal growth factor ("EGF") for 10 minutes before cell lysis. Lanes 1,2 show anti-Ras immunoprecipitates, lanes 3–6 show GST-RBD affinity precipitates, and lanes 5,6 show lysates which were preincubated with 4 µg of anti-Ras 238 (lane 5) or anti-Ras 259 (lane 6) before precipitation. EGF treatment of HeLa cells resulted in greatly increased Ras affinity precipitation by GST-RBD, while recovery of Ras in immunoprecipitates was unaltered by EGF treatment (FIG. 1b, lanes 1–4). In this experiment ~40–50% of total cellular Ras was activated by EGF treatment, in close agreement with the level of Ras-GTP measured previously by [32P] incorporation in EGF-stimulated Rat-1 fibroblasts (Hallberg et al., "Interaction of Ras and Raf in Intact Mammalian Cells Upon Extracellular Stimulation," J. Biol. Chem., 269:3913–16 (1994), which is hereby incorporated be reference). Anti-Ras antibody 259, which has been shown to block Ras-Raf interaction (Warne et al., "Direct Interaction of Ras and the Amino-Terminal Region of Raf-1 In Vitro," Nature, 364:352–55 (1993), which is hereby incorporated by reference), blocked EGF-stimulated Ras affinity precipitation, whereas antibody 238, which does not block Ras-Raf binding, did not (FIG. 1(b), lanes 5,6).

Co-immunoprecipatation of Ras and Raf after EGF treatment using either anti-Ras or anti-Raf antibodies under the conditions of this assay was not detected (data not shown), therefore endogenous Raf does not interfere with Ras-GTP binding to GST-RBD.

In FIG. 1(c), serum-starved HeLa cells were treated without (lanes 1–3) or with (lanes 4–7) 200 ng/ml EGF for 10 minutes then lysed in lysis buffer (lanes 1,4,7) or lysis buffer containing 1 mM GDP (lanes 2,5) or 0.1 mM GTP S (lanes 3,6) and precipitated with GST-RBD (lanes 1–6) or GST alone (lane 7). Inclusion of GDP or GTP in the lysis buffer did not affect affinity precipitation of Ras from EGF-treated or untreated cells (FIG. 1c, lanes 1–6) showing that GTP binding to Ras did not occur after lysis. In summary, the assay rapidly and specifically detects cellular Ras-GTP and changes in its levels in response to physiological stimuli.

Example 2

Ras is activated during G1 progression in HeLa cells

Figure 2C:
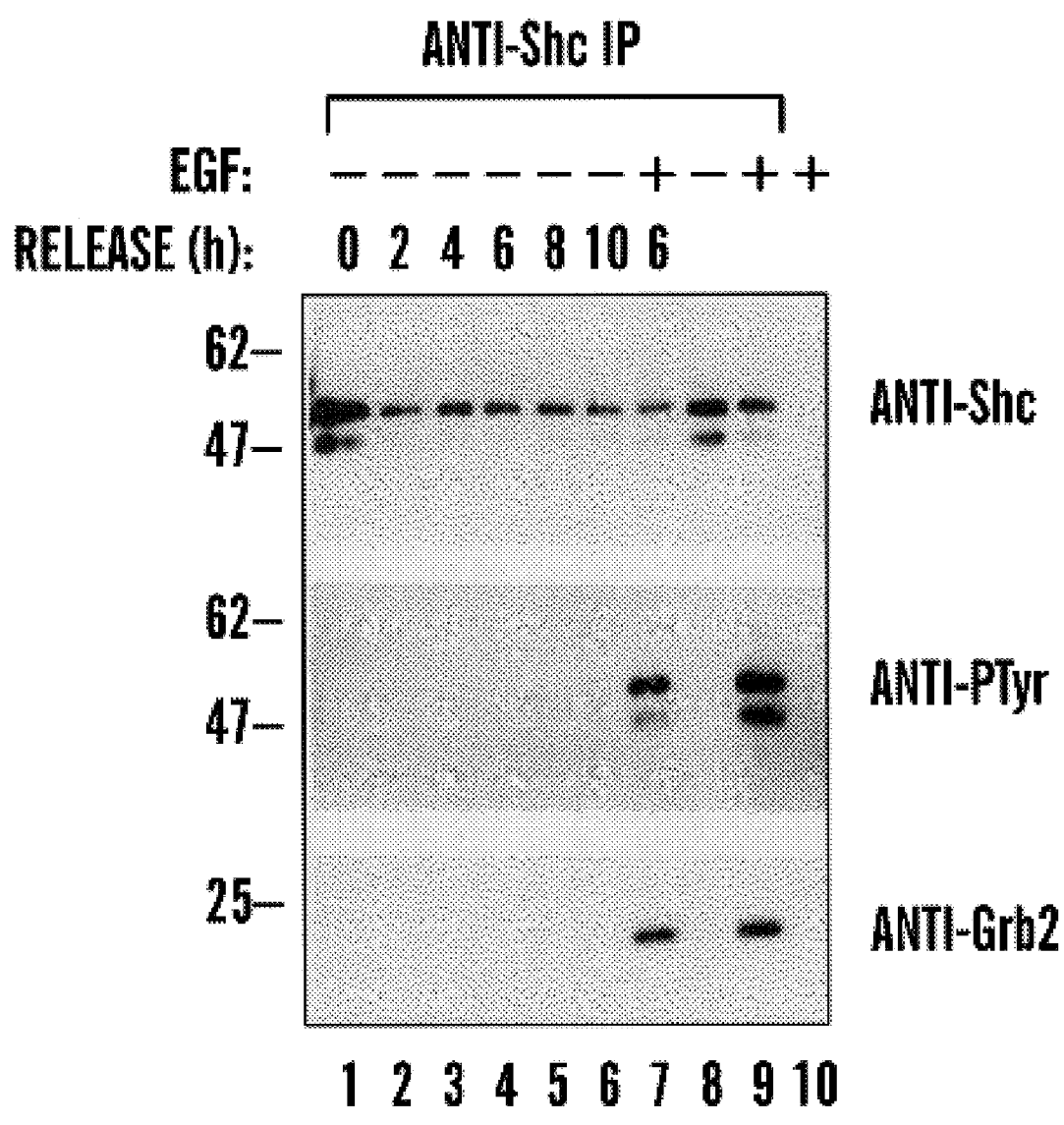

To evaluate whether Ras activity may be modulated during progression through G1 phase, HeLa cells were released from a mitotic arrest by means of a thymidine-nocodazole double block and released into G1 phase (in suspension culture unless otherwise indicated) or unsynchronized cells were serum-starved and treated with agonists. Shown are immunoblols probed with anti-Ras antibody. In FIG. 2(a), lanes 1–9 show GST-RBD affinity precipitates from cell lysates prepared at the indicated times after release from mitotic arrest, lanes 10–12 show affinity precipitates from unsynchronized (lane 10) or serum-starved cells treated without (lane 11) or with (lane 12) EGF (100 ng/ml for 10 minutes), lanes 13 and 14 show anti-Ras immunoprecipitate (lane 13) or whole cell lysate (lane 14) from 50% or 5% (relative to affinity precipitated) unsynchronized cell lysate. In FIG. 2(b), lanes 1–4 show affinity precipitates from cells released for 1 hours (lanes 1,2) or 6 hours (lanes 3,4) from mitotic arrest in suspension culture in the presence (lanes 2,4) or absence (lanes 1,3) of 10% calf serum ("CS"). Lanes 5–7 show affinity precipitates from cells released from mitotic arrest for 6 hours and allowed to attach to plates in the absence (lane 5) or presence of 25 μg/ml cycloheximide (lane 6) or 5 μg/ml actinomycin D (lane 7), added 45 minutes after release. Lanes 8–12 show affinity precipitates from serum-starved cells treated without (lane 8) or with 100 ng/ml EGF (lane 9), 10% serum (lane 10) or conditioned medium from lane 3 cells (lane 11) or lane 4 cells (lane 12) for 10 minutes. FIG. 2(c) shows anti-Shc immunoprecipitates from cells released from mitotic arrest for the indicated times (lanes 1–6), from 6 hours released cells treated with EGF (lane 7) or from serum-starved cells treated without (lane 8) or with (lanes 9,10) EGF. Lane 10 shows minus antibody control. Immunoblots were probed with antibodies against Shc, PTyr or Grb2.

The level of Ras-GTP increased several-fold following exit from mitosis, reaching a peak at about 4 hours into G1 phase, and then decreased as the cells approached S phase onset (about 10 hours after mitosis, as determined by cell sorting analysis) (FIG. 2a). Total levels of cellular Ras remained constant during this period (data not shown). The pattern and extent of mid-G1 phase Ras activation was the same whether cells were growing in the presence or absence of added serum (FIG. 2b, lanes 1–4; data not shown) and whether the cells were growing in suspension or attached to plates (lanes 4,5 and data not shown). Furthermore, G1 phase Ras activation was blocked by inhibitors of protein synthesis and gene transcription (FIG. 2b, lanes 5–7) and was not recapitulated by addition of mid-G1 conditioned medium to serum-starved cells (lanes 8,11,12). These results point towards a mechanism of Ras activation that is integral to the cell cycle machinery and not solely linked to receptor activation. The activation of Ras by EGF and many other agonists involves the binding of Grb2-Sos complexes to tyrosine phosphorylated Shc proteins. Treatment of serum-starved HeLa cells or cells synchronized in mid-G1 (6 hours mitotic release) with EGF resulted in rapid tyrosine phosphorylation of p46 and p52 Shc proteins (FIG. 2c, middle panel lanes 7,9). This was accompanied by Shc-Grb2 complex formation, shown by co-immunoprecipatation of Grb2 in anti-Shc immunoprecipitates (lower panel, lanes 7,9). However, there was no detectable tyrosine phosphorylation of Shc or binding to Grb2 associated with Ras activation during G1 progression (lanes 1–6). The mechanism of Ras activation in G1 phase, therefore, appears to differ from that used by EGF and many other mitogens to activate Ras.

Example 3
Activation of Ras in mid-G1 phase is uncoupled from Erk2 activation

Activation of Ras by growth factors leads to a rapid activation of the MAP kinases Erk1 and Erk2. Activated RasL61 has been shown to strongly activate co-expressed Erk2 in HeLa cells (Minden et al., "Selective Activation of the JNK Signalling Cascade and c-Jun Transcriptional Activity by the Small GTPases Rac and Cdc42Hs," Cell, 81:1147–57 (1995), which is hereby incorporated by reference). To determine whether Erk2 activity was stimulated in response to Ras activation during G1 progression, HeLa cell extracts were analyzed for Ras and Erk2 activity following mitotic release.

Figure 3A:
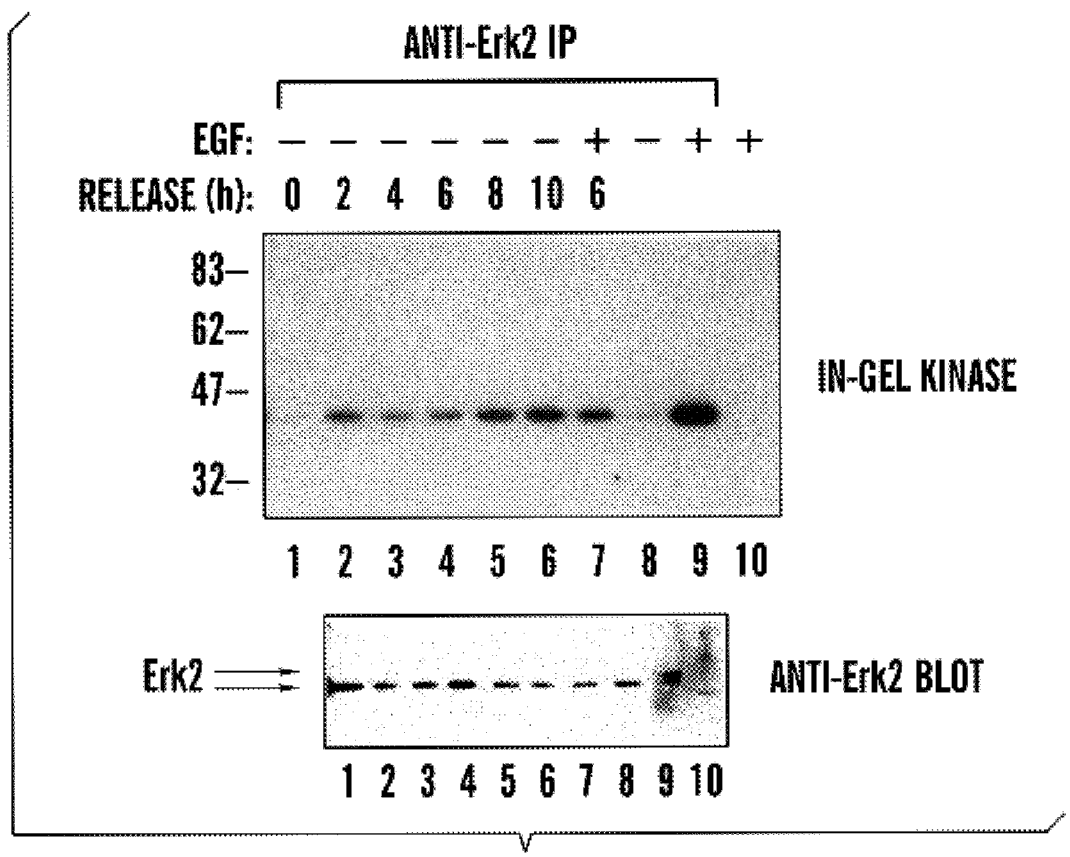
Figure 3B:
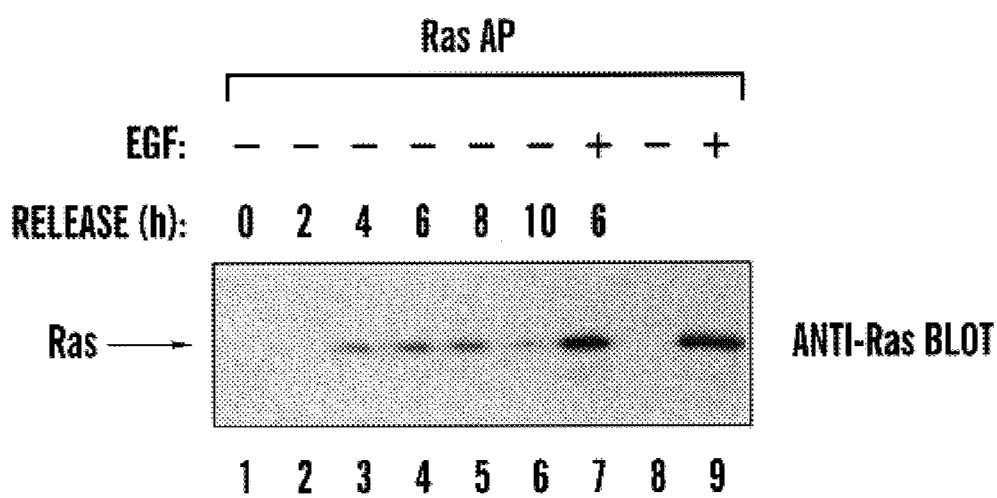

In FIG. 3(a), lanes 1–10 show anti-Erk2 immunoprecipitates from cells treated as described in lanes 1–10 in FIG. 2(c). Immunoprecipitates were subjected to in-gel kinase assay using myelin basic protein as substrate (upper panel) or immunoblotted with anti-Erk2 monoclonal antibody (lower panel). In FIG. 3(b), lanes 1–9 show GST-RBD affinity precipitates from cells in FIG. 3(a), lanes 1–9, immunoblotted with anti-Ras.

Erk2 kinase activity, measured by in-gel kinase assay of anti-Erk2 immunoprecipitates with myelin basic protein as a substrate, increased within 2 hours of release from mitosis and maintained about the same level of activity through G1 phase except for a small increase in activity near the G1/S transition (FIG. 3a, upper panel, lanes 1–9). In contrast, the level of Ras activation increased through early G1, again reaching maximal levels around mid-G1 (FIG. 3b). Interestingly, the activation of Erk2 by EGF in mid-G1 cells was substantially lower than the activation induced by EGF in serum-starved cells as determined by in-gel kinase (FIG. 3a, upper panel) and gel mobility shift (FIG. 3a, lower panel) assays (compare lanes 4 and 7 with 8 and 9), even though activation of Ras (FIG. 3b, lanes 4,7–9) and tyrosine phosphorylation of Shc (FIG. 2c) in response to EGF were similar in mid-G1 and serum-starved cells. Since only a small fraction of Erk2 was activated in G1, as indicated by the low level of the mobility-shifted form on immunoblots (FIG. 3a, lower panel), these results indicate that Ras activation was significantly uncoupled from Erk activation in mid-G1 phase.

Example 4
Ras is activated in mid-G1 in NIH 3T3 fibroblasts

Ras and Erk activities were examined during G1 progression in NIH 3T3 fibroblasts released from quiescence by serum treatment.

In FIG. 4(a), NIH 3T3 cells were serum-starved 24 hours and then treated without (lanes 2,11) or with 10% calf serum (lanes 3–10) or 100 ng/ml EGF (lane 12) for the indicated times. The upper panel shows GST-RBD affinity precipitates from cell lysates immunoblotted with anti-K-Ras antibody. Lane 1 contains whole cell lysate equivalent to 5% of precipitated. The lower panel shows cell lysates probed with an antibody specific for tyrosine phosphorylated, activated Erks 1 and 2 (New England Biolabs). In FIG. 4(b), NIH 3T3 cells were serum-starved and treated without (lane 1) or with 20% calf serum for 10 minutes (lane 2) or 4 hours (lane 3) or 50 ng/ml EGF (lane 4) or 10 ng/ml PDGF (lane 5) for 10 minutes. The upper panel shows GST-RBD affinity precipitates probed with anti-K-Ras. The middle and lower panels show anti-Erk2 immunoprecipitates probed with anti-Erk2 or anti-PTyr antibodies.

Under the conditions used, the cells entered S phase approximately 12 hours after serum addition, as determined by bromodeoxyuridine incorporation (data not shown). Levels of K-Ras (detected using a K-Ras-specific antibody which offers greater signal resolution in these cells) increased progressively during early G1, reaching maximal levels around 4 hours after serum addition and then decreasing towards basal levels as the cells approached S phase (FIG. 4a, upper panel). As in the mitotic release experiments, maxima activation of Erk1 and Erk2, as determined by immunoblotting of cell lysates with an antibody specific for tyrosine phosphorylated Erks, preceded peak K-Ras activation, occurring within 10 minutes of serum treatment (lower panel lanes 1,2). Thereafter, these activities decreased during early G1 progression (lanes 2–10), in agreement with other studies (Edelmann et al., "Cell Cycle Regulation of p70 S6 Kinase and p42/p44 Mitogen-Activated Protein Kinase in Swiss Mouse 3T3 Fibroblasts," *J. Biol. Chem.*, 271:963–71 (1996) and Bennett et al., "Multiple Requirements for SHPTP2 in Epidermal Growth Factor-Mediated Cel Cycle Progression," *Mol. Cell. Biol.*, 16:1189–1202 (1996), which are hereby incorporated by reference), such that activated Erks were barely detectable at the time of maximal K-Ras activation. Analysis of anti-Erk2 immunoprecipitates by gel mobility shift assay and anti-phosphotyrosine blotting (FIG. 4b) or in-gel kinase assay (data not shown) revealed substantial activation of Erk2 (>50% as determined by mobility shift) by serum, EGF or PDGF within 10 minutes which correlated with minor activation of K-Ras (lanes 1,2,4,5). In sharp contrast, only a small fraction of Erk2 was activated 4 hours after serum treatment when K-Ras was maximally activated (lanes 3).

Conclusions

The assay of the present invention rapidly and efficiently detects functionally active cellular Ras and should, therefore, find wide applicability in studies of normal and oncogenic Ras function. Its increased temporal resolution was exploited to measure Ras activation during G1 phase progressLon and to temporally correlate this with established upstream and downstream events in Ras signalling. Following release from mitosis, Ras became maximally activated in mid-G1. This activation was not associated with recruitment of Grb2 to Shc, was dependent on gene transcription and protein synthesis, and was apparently independent of extracellular soluble ligands, suggesting that Ras may be regulated by the cell cycle machinery as well as by receptor-mediated mechanisms. In serum-stimulated fibroblasts, K-Ras activation also reached a maximum in mid-G1. Importantly, this occurred after the largest increases in Erk activity, which occurred in very early G1, whether cells were released from mitosis or quiescence. This temporal disjunction between activation of Ras and a well established effector pathway raises the possibility that Ras targets other pathways in mid-G1 which may be required for progression into S phase. It has become clear that Ras utilizes multiple effectors to relay mitogenic signals to different cellular pathway (Marshall, C. J., "Ras Effectors," *Curr. Opin. Cell Biol.*, 8:197–204 (1996), which is hereby incorporated by reference). For instance, effector domain mutants of activated Ras have been identified that are defective for either Erk activation or cytoskeleton reorganization (Joneson et al., "Stimulation of Membrane Ruffling and MAP Kinase Activation by Distinct Effectors of RAS," *Science*, 271:810–12 (1996), which is hereby incorporated by reference). Neither type of mutant alone can stimulate DNA synthesis but together they promote progression into S phase. How these iistinct Ras effector pathways interact to result in mitogenesis is not yet clear. These pathways may be temporally coordinated by Ras in a cell cycle dependent manner.

Although preferred embodiments have been depicted and described in detail herein, it will be apparent to those skilled in the relevant art that various modifications, additions, substitutions, and the like can be made without departing from the spirit of the invention and these are therfore considered to be within the scope of the invention as defined in the claims which follow.

What is claimed:

1. A method for detecting activated ras protein, said method comprising; immobilizing on a solid support a ras effector protein or portion thereof comprising a ras binding region, wherein said ras effector protein is capable of relaying a mitogenic signal and wherein said ras effector protein or portion thereof binds with activated ras protein; incubating the immobilized ras effector protein or portion thereof comprising a ras binding region with lysates from cultured cells, wherein the lysates comprise activated ras protein; and determining the amount of activated ras protein bound to the immobilized ras effector protein or portion thereof.

2. The method according to claim 1, wherein the activated ras protein is bound to guanosine triphosphate.

3. The method according to claim 2, wherein the immobilized ras effector protein comprises a fusion protein.

4. The method according to claim 3, wherein the fusion protein comprises glutathione-S-transferase bound to a ras binding domain.

5. The method according to claim 4, wherein the ras binding domain is raf.

6. The method according to claim 5, wherein the ras binding domain comprises SEQ. ID. No. 2.

7. The method according to claim 4, wherein the fusion protein is produced using a pGEX-RBD plasmid.

8. The method according to claim 2, wherein the activated ras protein is H-ras, K-ras, or N-ras.

9. The method according to claim 1, wherein the cultured cells are human cultured cells.

10. The method according to claim 8, where the activated ras protein is human ras protein.

11. The method according to claim 1, wherein the determining comprises probing the activated ras protein with anti-ras antibodies or binding portions thereof.

12. The method according to claim 11, wherein the anti-ras antibodies are specific for H-ras, K-ras, or N-ras.

13. A method of detecting malignancy in a human subject comprising:
    collecting a cell culture from the human subject;
    providing lysates from the cell culture;
    incubating the lysates with an immobilized ras effector protein or portion thereof wherein said ras effector protein is capable of relaying a mitogenic signal and wherein said ras effector protein or portion thereof binds with activated ras protein; and
    determining the amount of activated ras protein bound to the immobilized ras effector protein.

14. The method according to claim 13, wherein the activated ras portein is bound to guanosine triphosphate.

15. The method according to claim 14, wherein the ras effector protein comprises a fusion protein.

16. The method according to claim 15, wherein the fusion protein comprises glutathione-S-transferase bound to a ras binding domain.

17. The method according to claim 16, wherein the ras binding domain is raf.

18. The method according to claim 17, wherein the ras binding domain comprises SEQ ID. No. 2.

19. The method according to claim 16, wherein the fusion protein is produced using a pGEX-RBD plasmid.

20. The method according to claim 14, wherein the activated ras protein is H-ras, K-ras, or N-ras.

21. The method according to claim 13, wherein the determining comprises probing the activated ras protein with anti-ras antibodies or binding portions thereof.

22. The method according to claim 21, wherein the anti-ras antibodies are specific for H-ras, K-ras, or N-ras.

23. The method of claim 1 wherein the ras effector protein is at least one of phosphatidylinositol-3-kinase, Ral guanine nucleotide exchange factors (RalGDS), Rgl, Rlf, p12-RasGaP, neurofibromin, or Rin.

24. The method of claim 13 wherein the ras effector protein is at least one of phosphatidylinositol-3-kinase, Ral guanine nucleotide exchange factors (RalGDS), Rgl, Rlf, p12-RasGaP, neurofibromin, or Rin.

* * * * *